(12) United States Patent
Ait Ikhlef et al.

(10) Patent No.: US 6,855,736 B2
(45) Date of Patent: Feb. 15, 2005

(54) MOLECULAR TARGET OF NEUROTOXICITY

(75) Inventors: Ali Ait Ikhlef, Alfortville (FR); Annelies Resink, Paris (FR); Fabien Schweighoffer, Vincennes (FR)

(73) Assignee: Exonhit Therapeutics SA, Paris (FR)

( * ) Notice: Subject to any disclaimer, the term of this patent is extended or adjusted under 35 U.S.C. 154(b) by 0 days.

(21) Appl. No.: 09/983,754

(22) Filed: Oct. 25, 2001

(65) Prior Publication Data

US 2003/0064374 A1 Apr. 3, 2003

(30) Foreign Application Priority Data

Aug. 14, 2001 (FR) ............................................. 01 10819

(51) Int. Cl.[7] .................... A61K 31/135; A61K 31/522; A61K 31/425
(52) U.S. Cl. ............. 514/648; 514/263.34; 514/263.36; 514/263.38; 514/369
(58) Field of Search ........................... 514/44; 435/325, 435/6, 375; 536/24.5, 23.1, 24.3

(56) References Cited

PUBLICATIONS

Brighina et al. Recent Advances in the Therapy of Amyotropic Lateral Sclerosis: Focus on Excitotoxicity. Functional Neurology, 2001 vol. 16 (SUPPL): 189–202.*
H Dinter, BioDrugs,"Phosphodiesterase Type 4 Inhibitors, "Feb. 2000, 13 (2)pp. 87–94.*
LW Myers et al., American Academy of Neurology,"Pentoxifylline is not a promising treatment for multiple sclerosis in progression phase," 1998, 51: pp. 1483–1486.*
AD Branch, TIBS, "A good antisense molecule is hard to find," Feb. 1998, pp. 45–50.*
ST Crooke, Basic Principles of Antisense Therapeutics, 1998, Chap. 1, pp. 1–50.*
K Pihl–Casey, BioWorld Today, "Isis to Restructure as Crohn's Disease Drug Fails in Phase III," Dec. 1999, vol. 10,No. 239, pp. 1–2.*
K–Y Jen et al., Stem Cells, "Suppression of Gene Expression by Targeted Disruption of Messenger RNA: Available Options and Current Strategies," 2000, 18: 307–319.*
BME van Oosten et al., Journal of Neuroimmunology, "A pilot study investigating the effects of orally administered pentoxifylline on selected immune variables in patients with multiple sclerosis," 1996, 66, pp. 49–55.*
JE Friedman et al., Archives of Neurology, "Pseudocervical Cord Syndrome: A Deceptive Flumazenil Reversible Manifestation of Hepatic Encephalopathy," Oct. 1996, vol. 53, pp. 956–957.*
Asahara et al. Glutamate enhances phosphorylation of neurofilaments in cerebellar granule cell culture. Journal of the Neurological Sciences, 1999 vol. 171:84–87.*
Santos et al. Cyclic AMP increases the survival of ganglion cells in mixed retinal cell cultures in the absence of exogenous neurotrophic moleucles . . . Brazilian Journal of Medical and Biological Research, 2001, vol. 34:1585–1593.*
Snider et al. Signaling the Pathway to Regeneration. Neuron, 2002 vol. 35:13–16.*
Feldman et al. Breathing: Rhythmicity, Plasticity, Chemosensitivity. Annual Review of Neurosciences, 2003 vol. 23:239–266.*

* cited by examiner

Primary Examiner—Karen A. Lacourciere
Assistant Examiner—Terra C. Gibbs
(74) Attorney, Agent, or Firm—Nixon & Vanderhye P.C.

(57) ABSTRACT

The present invention relates to the fields of biology, genetics and medicine. In particular it concerns new methods for the detection, characterization and/or treatment (or management) of neuro degenerative diseases, particularly amyotrophic lateral sclerosis.

7 Claims, 3 Drawing Sheets

MOLECULAR TARGET OF NEUROTOXICITY

DESCRIPTIVE SUMMARY

The present invention relates to the fields of biology, genetics and medicine. In particular it concerns new methods for the detection, characterisation and/or treatment (or management) of neurodegenerative diseases, particularly amyotrophic lateral sclerosis. The invention equally concerns methods for identifying or screening compounds, genes, cells, plasmids or compositions useful for implementing the hereinabove methods. The invention describes in particular the role of PDE4B in these diseases and its use as therapeutic, diagnostic or experimental target.

The present invention relates to the fields of biology, genetics and medicine. In particular it concerns new methods for the detection, characterisation and/or treatment (or management) of neurodegenerative diseases, particularly amyotrophic lateral sclerosis. The invention equally concerns methods for identifying or screening compounds active in these diseases. The invention further concerns the compounds, genes, cells, plasmids or compositions useful for implementing the hereinabove methods. The invention derives notably from the identification of the role of phosphodiesterase 4B in these diseases and describes its use as target or therapeutic, diagnostic or experimental marker in these disorders.

Many neurodegenerative diseases have been described as having a component or a stage linked to the phenomenon of excitotoxicity. Such is the case for Alzheimer's disease, Parkinson's disease, multiple sclerosis and Huntington's chorea.

Amyotrophique lateral sclerosis (or ALS) is a neurodegenerative disease accompanied by different types of inclusions such as Lewis bodies and characterised by apoptosis of spinal and cortical motor neurons whose death is sometimes associated with frontal dementia. Sporadic forms for which no mutation has been described exist alongside familial forms (FALS) associated with mutations in the SOD1 gene encoding superoxide dismutase. The majority of cases is sporadic, familial forms (FALS) being very rare. It is likely that a long, asymptomatic period precedes the onset of clinical symptoms, which are variable and difficult to classify. Future advances in therapy will make it possible to replace symptomatic treatments with strategies based on the molecular causes of the disease At the cellular level, these symptoms are related to death of cortical motor neurons and spinal motor neurons. This neuronal death has been linked to different phenomena which underly a number of neurodegenerative diseases. Such is the case of excitotoxicity linked to glutamate, oxidative stress, auto-immunity directed against neuronal markers (calcium channels in the case of ALS) as well as cytoskeletal abnormalities. Although such phenomena are known, the cause or causes of these diseases, including ALS, remain obscure. Even though FALS is related to mutations in the SOD1 gene coding for superoxide dismutase, the mechanisms by which neurons become committed towards cellular death, of which at least one component is apoptosis, are unknown.

Elucidating the molecular events involved in the different phenomena implicated in cell death will allow the development of new therapeutic strategies. The study of these events is difficult to carry out using human biopsy specimens. Such biopsies obviously come from post-mortem samples whose quality is difficult to control and which reflect only the pathological states present at the late stages of the disease.

Animal models give access to biological samples that allow the different steps of disease development to be analysed and compared with healthy controls. In this respect, transgenic mice expressing the human SOD1 gene bearing one of the mutations prevalent in FALS (mutation G93A) are available from Jackson Laboratory, on condition that a user's licence is obtained from Northwestern University. This model reproduces in 120 days the fatal outcome of the disease with symptoms similar to those in the human disease. The onset of ALS symptoms related to mutation G93A in the SOD1 gene does not result from a reduction in superoxide dismutase activity but rather a gain in function which increases the ability of the enzyme to generate free radicals. Despite this knowledge, the molecular events governing the different stages of ALS are poorly understood. The complexity of these molecular events reflects the progression of the disease: in the transgenic model studied, no neuronal deregulation or clinical manifestations are observed at 30 days. Sixty days is a stage shortly before symptom onset, but which is already characterised in brain by changes in cellular physiology such as alteration of mitochondrial metabolism, stress and neuronal death associated with an excitotoxicity phenomenon. At 90 days, 50% of cortical and spinal motor neurons are dead and an active process of neuronal apoptosis begins in parallel to activation of astrocytes. The phenomenon of excitotoxicity is no longer observed at this stage. Neuronal death is associated with activation of caspases which do not appear to be involved in the early stages of the disease.

Elucidating the different molecular events specific of the different stages of the disease should allow identification of new therapeutic targets as well as new diagnostic markers. One of the most effective approaches to carry out this identification consists in identifying the genes and proteins whose expression characterises a pathophysiological state.

The present invention now describes the identification of genetic events involved in the phenomena of excitotoxicity and neuronal death. The present invention thus provides new therapeutic and diagnostic approaches to the diseases associated with these phenomena, as well as new targets for identifying active compounds.

More specifically, a qualitative differential analysis has been carried out on RNA extracted from brain and spinal cord samples without preliminary isolation of neurons in order to take into account a maximum of alternative splicing events related to disease development. This analysis was carried out by qualitative differential screening according to the DATAS method (described in application No. WO99/46403), which has unequalled advantages.

The present patent application is derived notably from the applicant's construction of a repertoire of alternative splicings in the brains of 60-day-old animals in the ALS model. This repertoire containing more than 200 separate sequences involves key players in the excitotoxicity phenomenon, such as potassium channels and the NMDA receptor. Sequences derived from RNAs coding for proteins involved in the response to stress, including heat shock proteins, are also part of this repertoire, underscoring the role of this latter response in the early stages of ALS. Altered energy metabolism clearly appears to affect cortical motor neurons of animals that develop the disease. For instance, intron 6 of mitochondrial creatine kinase is isolated specifically from messenger RNAs expressed in pathological conditions in 60-day-old animals. Interruption of the coding sequence by retention of this intron results in a messenger RNA that encodes an inactive form of the enzyme. This observation agrees with biochemical findings showing a reduction of mitochondrial creatine kinase activity correlated with a reduction in the amount of this enzyme in neurons from animals in the same transgenic model.

The specificity of the sequences making up this repertoire is confirmed by the fact that the same qualitative differential analysis of gene expression performed in 90-day-old animals leads to a different repertoire in which, in particular, the different markers of excitotoxicity are absent. Analysis of splicing modifications confirms that the molecular events differ according to the stage of the disease.

The use of DATAS on RNA from 60-day-old transgenic and control animals has led to the isolation of a cDNA fragment derived from the mRNA of phosphodiesterase 4B. Such fragment corresponds to an exon fragment specifically present in control animals and therefore specifically deleted in SOD1G93A transgenic animals at the 60 day stage. Such fragment spans nucleotides 377 to 486 numbered from the mouse PDE48 stop codon (SEQ ID NO:1) (sequence also accessible in GenBank, No. AF208023). This sequence comprises 2912 bases, the deleted fragment corresponding to bases 2760 to 2869. This is a noncoding region and is differentially expressed in control animals and transgenic animals due to the alternative use of a noncoding 3' exon or due to the use of two alternative polyadenylation sites. This differential expression has been demonstrated by the RT-PCR experiments presented in FIGS. 1 and 2.

The present application therefore demonstrates the involvement of phosphodiesterase 4B in the development of excitotoxicity processes and neuronal death. The results obtained reveal a higher level of expression of PDE4B in pathological nerve tissue, in relation to a structural modification of the corresponding RNA, more particularly a deletion of a region in the 3' noncoding part. This result is altogether compatible with the presence of mRNA destabilisation sequences in the sequence identified by DATAS. Their deletion in PDE4B mRNA, through splicing or through the use of alternative polyadenylation sequences, can result in stabilisation, therefore in an increased expression of the coding portion of this RNA. This event occurs specifically in the brain of transgenic animals and not in control animals. The present invention therefore describes an original molecular event leading to increased expression of PDE4B mRNA in the brain of transgenic animals and which is correlated over time with the phenomenon of excitotoxicity and/or neuronal death. The invention further shows, for the first time, that increased expression of PDE4B is associated with the early stages of ALS. PDE4B is therefore a new and important therapeutic target in the development of treatments for these diseases, of particular use in the early stages of their development, and addressing the true molecular bases of the disease and not the accompanying symptoms or inflammatory components. The invention also provides for new methods of diagnosis, screening, detection, determination of a predisposition or monitoring the progression or the efficacy of treatment of these diseases.

One object of the invention is therefore to provide a method for detecting an excitotoxicity situation or neuronal stress in a subject, comprising measuring in vitro the expression of phosphodiesterase 4, particularly phosphodiesterase 4B, in a sample from the subject. The method advantageously comprises measuring the differential expression of the 3' noncoding region of the PDE4B gene and the rest of the gene, particularly the coding portion.

A further object of the invention is therefore to provide a method for detecting an excitotoxicity situation or neuronal stress in a subject, comprising detecting the presence of a mutant RNA of phosphodiesterase 4, particularly phosphodiesterase 4B, in a sample from the subject, in particular a form deleted of all or part of the 3' noncoding region.

Another object of the invention is the use of a nucleic acid comprising all or part of a sequence derived from the PDE4B gene or messenger RNA for implementing a method for diagnosis or detection of a situation of neuronal stress and more specifically an excitotoxicity situation.

The invention is generally based on the use of a nucleic acid complementary to all or part of the PDE4B gene or messenger, for detecting pathological events related to excitotoxicity, stress, neuronal death, etc.

More specifically, these are nucleic acids capable of demonstrating a deleted form of PDE4B mRNA, particularly a form deleted of all or part of the 3' noncoding region. A specific example is the use of a nucleic acid complementary to all or part of the region located between residues 2760 to 2869 of sequence SEQ ID No. 1, or corresponding residues of the sequence of the human PDE4B gene or mRNA. The cDNA sequence encoding human PDE4B and the corresponding protein are shown in sequences SEQ ID No. 3 and 4 (also see Genbank, No. NM_002600). The 3' noncoding region of the human PDE4B gene or RNA corresponds to residues 2461 to 4068 of SEQ ID No.: 3.

The invention has applications in the diagnosis or detection of different pathologies involving excitotoxicity phenomena, such as Alzheimer's disease, Parkinson's disease, multiple sclerosis, Huntington's chorea or cerebral ischemia. It may be used for early detection, to demonstrate a predisposition, to guide the choice and adaptation of a treatment, to monitor disease progression, etc. It is especially suited to detecting multiple sclerosis at an early stage.

Phosphodiesterases hydrolyse cyclic nucleic acids such as cAMP and cGMP, regulating different signalling cascades. PDE4B hydrolyses cAMP, thereby regulating the concentrations of this second messenger inside the cell. The role of cAMP in the balance between cell viability and apoptosis has been well described in the literature. In particular, the cAMP cascade plays an integral role in cell survival cascades involving kinases like Akt and PI3K as well as in regulating the activity of transcription factor CREB. It is noteworthy that this transcription factor is involved in neuron survival and neurite growth. Nonetheless, the use of PDE and, advantageously, PDE4 inhibitors has never been envisioned to improve neuron viability and more particularly to protect them against excitotoxicity. It has been suggested that PDE4 inhibitors, developed to inhibit inflammatory phenomena, may potentially be useful in neurodegenerative diseases such as Alzheimer's disease. This suggestion is based on the goal of reducing the inflammation observed in brain during neurodegenerative processes and not at all on a rationale aiming to directly inhibit neuronal death.

The present invention provides the molecular basis that justifies the use of PDE4 inhibitors for the treatment of ALS and more generally for improvement of neuron viability during excitotoxicity phenomena, in particular starting from the early stages of these diseases.

As a matter of fact the invention demonstrates the existence of splicing events and alternative polyadenylation sites affecting the PDE4B gene, associated with the development of neuronal excitotoxicity, and provides for methods to detect or screen for dysfunctions based on demonstrating the presence of such spliced forms in biological samples.

In an advantageous manner, the nucleic acid used (as probe) comprises all or part of the sequence coding for the 3' noncoding region of the PDE4B gene or RNA located between nucleotides 2384 and 2869 of the sequence SEQ ID NO.: 1 or between nucleotides 2461 and 4068 of the sequence SEQ ID NO: 3 or a sequence complementary thereto.

According to specific embodiments, the invention makes use of a nucleic acid complementary to a region located within one of the following sequences:

residues 2384 to 2869 of SEQ ID NO 1
residues 2500 to 2869 of SEQ ID NO 1
residues 2760 to 2869 of SEQ ID NO 1
residues 2780 to 2850 of SEQ ID NO 1
residues 2790 to 2810 of SEQ ID NO 1
residues 2600 to 4040 of SEQ ID NO 3
residues 3000 to 4040 of SEQ ID NO 3
residues 3500 to 4040 of SEQ ID NO 3
residues 3900 to 4040 of SEQ ID NO 3.

In another specific embodiment, one uses a nucleic acid complementary to the sequence of the PDE4 RNA region resulting from deletion of all or part of the 3' noncoding region. Deletion of a domain in fact creates new junctions in the sequence, which are specific of the deleted form and may be used to demonstrate the presence of such a form in a sample.

Preferably, the degree of complementarity is perfect so as to ensure better specificity of hybridisation. However, it is understood that some mispairing may be tolerated. The nucleic acid used for implementation of the methods hereinabove may be a DNA or an RNA, preferably a synthetic DNA. It preferably comprises 10 to 500 bases, typically 10 to 100 bases. It is understood that a longer nucleic acid may be used, if desired, although this is not preferred. The nucleic acid is advantageously a single stranded DNA, from 10 to 500 bases, complementary at least to a region of the 3' noncoding sequence of PDE4B. The nucleic acid may be labelled, for instance by radioactivity, enzymatic, luminescent, fluorescent, chemical means, etc.

To implement the methods according to the invention, a biological sample from a subject, containing a nucleic acid, is placed in contact in vitro with a nucleic acid such as defined hereinabove, and the formation of a hybrid is detected. The biological sample may be a sample of blood, fluid, cell, tissue, etc. The nucleic acid may be immobilised on a support of the type glass, silica, nylon, etc.

The process of detection, screening or diagnosis may be implemented by using different types of samples from a subject, such as for instance tissue biopsies, particularly nerve tissue. In an especially surprising and advantageous manner, the present invention further shows that deregulation of PDE4 expression, correlated with the excitotoxicity phenomenon, may be directly demonstrated in muscle tissue. This is especially remarkable in the case of neurodegenerative 10 diseases such as ALS.

During the development of ALS, degenerative phenomena occur not only in brain but also in the spinal cord and consequently in muscle through defective innervation. FIG. 2 depicts the modifications of PDE4B mRNA expression in muscle from control and transgenic mice, detected by using the same PCR primers as in the experiment on RNA from the brains of these same animals. In an analogous, but less pronounced manner, a reduction in the expression of the 3' noncoding region of PDE4B, and not in the remainder of this mRNA (particularly the coding portion), is observed specifically in muscle of animals at the end of the presymptomatic stage, i.e. aged 90 days.

One difficulty encountered in the study and treatment of ALS is that of establishing an early diagnosis. The observation that PDE4B mRNA is deregulated in ALS muscle makes it possible to establish an early diagnosis from muscle biopsies of patients. Such diagnosis is based on the detection of differential expression between the 3' noncoding region and the rest of the sequence, particulary the coding portion, of PDE4B.

A specific method for detecting a situation of neuronal stress, notably excitotoxicity, in particular linked to a neurodegenerative disease in a subject, comprises measuring PDE4B gene expression or the presence of deleted forms of the PDE4B messenger, in a sample of muscle cells from said subject.

To measure differential expression, one uses for example a probe corresponding to (that is to say, specific of) a part of the 3' noncoding region and a probe corresponding to a part of the coding region of PDE4B. The signal detected with each of these probes allows an evaluation of differential expression. Another approach makes use of two primer pairs allowing amplification of a portion of the 3' noncoding region on the one hand and a portion of the coding region on the other hand. Typically, PDE4B expression, or differential expression, or the presence of an altered form, can be determined by conventional techniques of molecular biology, such as for example sequencing, hybridisation, amplification, RT-PCR, migration on gels, etc.

In this regard, one object of the invention is based on a primer complementary to a portion of the PDE4B 3' noncoding region, and allowing amplification of a part of this region. The primer advantageously comprises 8 to 20 bases. It is preferably composed of a fragment of 8 to 20 consecutive residues of the sequence located between nucleotides 2386 and 2869 of sequence SEQ ID NO :1 or between nucleotides 2461 and 4068 of the sequence SEQ ID NO: 3 or a sequence complementary thereto. A further object of the invention is a primer pair allowing specific amplification of at least part of the PDE4 3' noncoding region, said pair comprising at least one primer such as defined hereinabove.

An additional object is a kit for analysing PDE4 expression, particularly the differential expression between the 3' noncoding region and the coding region, the kit comprising a nucleotide probe specific of a part of the sequence of the 3' noncoding region and a nucleotide probe specific of a part of the sequence of the coding region.

A further object is a kit for analysing PDE4 expression, particularly the differential expression between the 3' noncoding region and the coding region, the kit comprising a pair of nucleotide probes allowing specific amplification of at least part of the 3' noncoding region of PDE4 and a pair of nucleotide probes allowing specific amplification of at least part of the coding region of PDE4.

One other object of the invention is based on the use of a compound capable of inhibiting or reducing the expression or activity of PDE4B, in order to prepare a composition designed to treat neurodegenerative diseases, notably in early stages, more preferably to reduce the early neuronal excitotoxicity associated with neurodegenerative diseases such as ALS, Alzheimer's disease or Parkinson's disease.

Within the context of the invention, the term "treatment" refers to preventive, curative, palliative treatment, as well as management of patients (alleviating suffering, improving life expectancy, slowing disease progression), etc. The treatment may furthermore be conducted in combination with other agents or treatments, especially addressing late events in the disease, such as caspase inhibitors or other active compounds.

Another object of the invention is the use of a compound capable of inhibiting (preferably in a selective manner) the expression or activity of PDE4B of sequence SEQ ID NO: 2 or 4 in order to prepare a composition designed to reduce neuronal excitotoxicity.

A further object of the invention is a method for treating a disease associated with neuronal stress, particularly excitotoxicity, comprising administering to a subject a compound that inhibits PDE4B activity or expression, preferably a compound that selectively inhibits PDE4.

The compound used may be any compound that can inhibit the expression of PDE4, particularly PDE4B, i.e. in particular any compound inhibiting gene transcription, RNA maturation, RNA translation, posttranslational protein modification, etc. It may be a compound inhibiting RNA modification, notably the deletion of part of the 3' noncoding region.

In a specific embodiment, the compound is an antisense nucleic acid, capable of inhibiting transcription of the PDE4B gene or translation of the corresponding mRNA. The antisense nucleic acid may comprise all or part of the sequence of the PDE4B gene, a fragment thereof, the PDE4B messenger, or a sequence complementary thereto. The antisense nucleic acid may notably comprise a region complementary to the sequence located between residues 218 to 2383 of SEQ ID NO:1 or 766 to 2460 of SEQ ID NO: 3, and inhibit (or reduce) its translation into protein. The antisense nucleic acid may be a DNA, an RNA, a ribozyme, etc. It may be single-stranded or double-stranded. It may also be an RNA encoded by an antisense gene. Where it is an antisense oligonucleotide, it typically contains fewer than 100 bases, for example on the order of 10 to 50 bases. Such oligonucleotide may be modified to improve its stability, its resistance to nucleases, its penetration into the cell, etc.

According to another embodiment, the compound is a chemical compound of natural or synthetic origin, particularly an organic or inorganic molecule, of plant, bacterial, viral, animal, eukaryotic, synthetic or semi-synthetic origin, capable of modulating the expression or activity of PDE4B. Pentoxifylline and etazolate may be cited as a preferred and non-limiting example.

According to a further embodiment, it may be a peptide, for example comprising a region of the PDE4 protein (notably PDE4B) and able to antagonise its activity.

The present invention therefore proposes, for the first time, PDE4B as a therapeutic target for the treatment of molecular events associated with excitotoxicity. According to specific embodiments, the invention may be used to inhibit or reduce neuronal excitotoxicity in early stages of neurodegenerative diseases. It finds applications particularly in the treatment of Alzheimer's disease, Parkinson's disease, multiple sclerosis, Huntington's chorea and cerebral ischemia.

Other objects of the invention are based on:
use of the hereinabove compounds for the treatment of ALS, notably to reduce neuronal excitotoxicity in the early stage of ALS,
use of pentoxifylline for preparation of a composition designed to inhibit PDE4B activity in patients with ALS, or
use of etazolate for preparation of a composition designed to inhibit PDE4B activity in patients with ALS.

The invention equally concerns methods of treatment of ALS comprising administering a compound that selectively inhibits the expression or activity of PDE4B of sequence SEQ ID NO: 2 or 4. Preferably, the methods of the invention are used for treatment in the early stage of neurodegenerative diseases.

The administration may be performed by any method known to those skilled in the art, preferably by injection, typically by the intraperitoneal, intracerebral, intravenous, intraarterial or intramuscular route. The injected doses may be adapted by those skilled in the art. Typically, approximately 0.01 mg to 100 mg/kg are injected, for inhibitor compounds that are chemical in nature. For nucleic compounds, doses may range for example from 0.01 mg to 100 mg per dose. It is understood that repeated injections may be given, possibly in combination with other active agents or any pharmaceutically acceptable vehicle (eg., buffers, saline solutions, isotonic, in the presence of stabilisers, etc.).

The invention may be used in mammals, notably in human beings. The results presented in the examples illustrate the efficacy of PDE4B inhibitors in improving the viability of neurons placed in excitotoxicity conditions.

Other objects of the invention concern methods for selecting, identifying or characterising compounds active in diseases associated with excitotoxicity, or neuronal stress, comprising placing test compounds in contact with a cell expressing PDE4B (particularly a variant devoid of the 3' noncoding region), and identifying compounds inhibiting the expression or activity of this protein.

The methods may be used with different cell populations, such as primary cells or cell lines of mammalian origin (human, murine, etc.). Advantageously, cells which do not naturally express PDE4B, transfected with a nucleic acid coding the desired variant, are used. In this manner, the selectivity of the method is increased. Lower eukaryotic cells (yeasts, etc.) or prokaryotic cells may also be used.

The screening methods may also be carried out in an acellular system, by measuring the capacity of test compounds to bind PDE4B or a variant or fragment thereof.

Another object of the invention concerns any nucleic acid coding a polypeptide such as defined hereinabove, vectors containing it, recombinant cells, and utilisations. The vectors may be plasmids, phages, cosmids, viruses, artificial chromosomes, etc. Preferred vectors are exemplified by plasmid vectors, such as those derived from commercially available plasmids (pUC, pcDNA, pBR, etc.). Such vectors advantageously contain a selection gene and/or an origin of replication and/or a transcriptional promoter. Other specific vectors are for example viruses or phages, particularly replication-defective recombinant viruses, such as viruses derived from retroviruses, adenoviruses, AAV, herpes virus, baculovirus, etc. The vectors may be used in any competent host, such as for example prokaryotic or eukaryotic cells. These may be bacteria (*E. coli* for example), yeasts (Saccharomyces or Kluyveromyces, for example), plant cells, insect cells, mammalian cells, notably human, etc. These may be cell lines, primary cells, mixed cultures, etc.

Other aspects and advantages of the present invention will become apparent from the following examples which are given for purposes of illustration and not by way of limitation.

EXAMPLES

Figure 1:
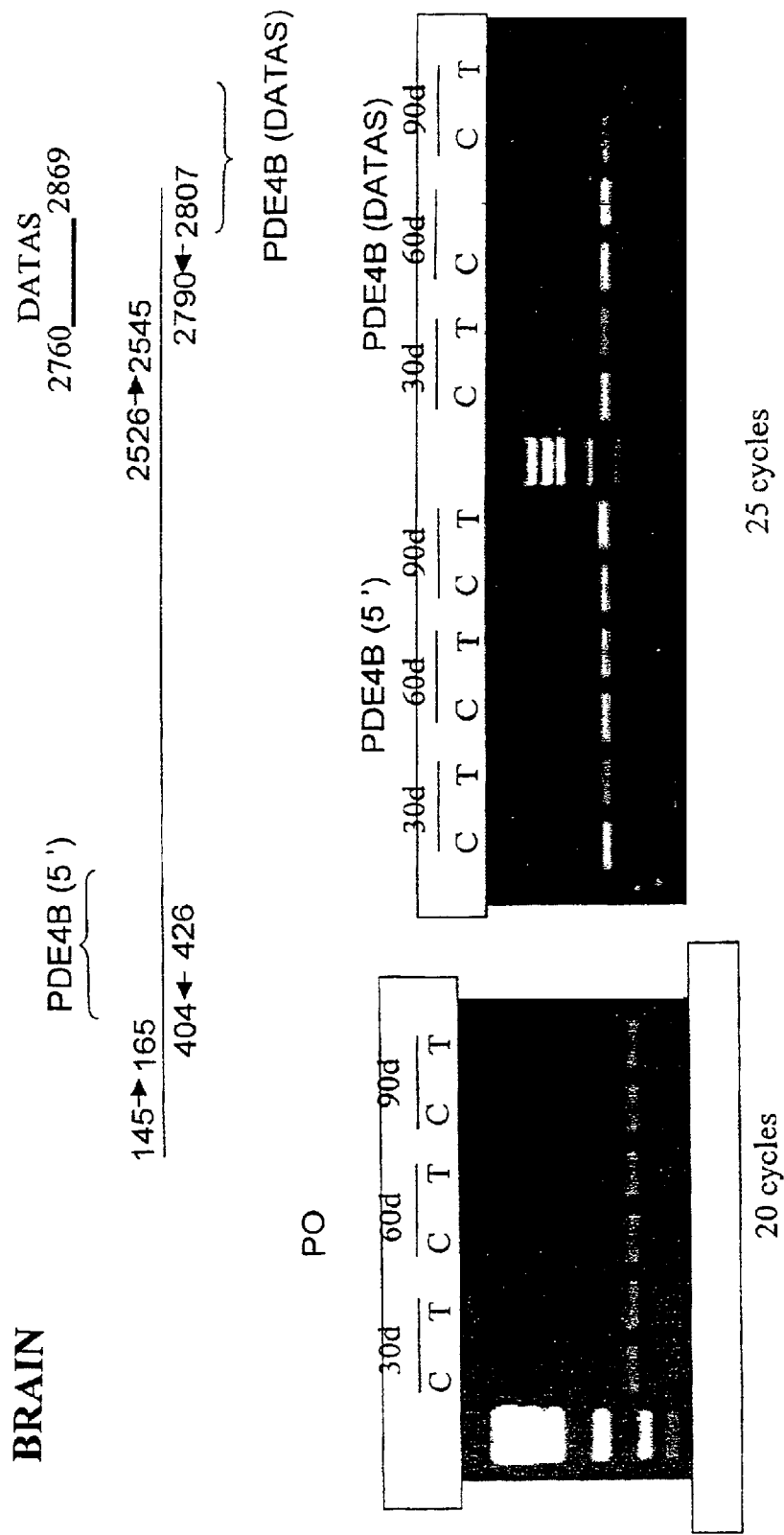
FIG. 1: Semi-quantitative PCR of PDE4B on brain specimens.

Example 1
Identification of PDE4 as Molecular Target of Excitotoxicity

Qualitative differential analysis was carried out on polyadenylated (poly A+) RNA extracted from brain specimens of animals at different stages, without preliminary isolation of neurons so as to take into account a maximum of alternative splicing events linked to disease development.

Poly A+RNAs are prepared by methods known to those skilled in the art. This may be in particular a treatment by means of chaotropic agents such as guanidium thiocyanate followed by extraction of total RNA by means of solvents (phenol, chloroform for example). Such methods are well known to those skilled in the art [see Maniatis et al., Chomczynsli et al., Anal. Biochem. 162 (1987) 156], and may be easily practised by using commercially available kits. Poly A+RNAs are prepared from these total RNAs according to conventional methods known to those skilled in the art and provided in commercially available kits. These poly A+RNAs serve as template for reverse transcription reactions using reverse transcriptase. In an advantageous manner, reverse transcriptases devoid of RNase H activity are used, so as to obtain initial complementary DNA strands that are larger in size than those obtained with conventional reverse transcriptases. Such RNase H-free reverse transcriptase preparations are commercially available.

At each time point in disease development (30 days, 60 days and 90 days), the poly A+RNAs as well as the single-stranded cDNAs are prepared from transgenic animals (T) and syngeneic control animals (C).

In accordance with the DATAS method, for each time point hybridisations are carried out of mRNA (c) with cDNA (T), and reciprocal hybridisations of mRNA (T) with cDNA (C).

The mRNA/cDNA heteroduplexes are then purified according to the protocols of the DATAS method.

RNA sequences not paired with a complementary DNA are released from these heteroduplexes through the action of RNAse H, as this enzyme degrades paired RNA sequences. Such unpaired sequences represent qualitative differences existing between RNAs which by the way are homologous between themselves. These qualitative differences may be located anywhere on the RNA sequence, at the 5' or 3' region or inside the sequence and notably in the coding sequence. Depending on their location, these sequences may not only be alternative splicing, but also may be the result of translocations or deletions.

The RNA sequences representing qualitative differences are then cloned according to methods known to those skilled in the art and more specifically those described in the patent for the DATAS method.

Such sequences are gathered together in cDNA banks which constitute qualitative differential banks. One such bank contains the exons and introns specific of the healthy situation; the other banks contain the splicing events characteristic of the pathological conditions.

Differential expression of the clones was checked by hybridisation with probes obtained by reverse transcription of messenger RNAs extracted from the different situations under study. Clones showing differential hybridisation were retained for subsequent analysis. The sequences identified by DATAS correspond to introns and/or exons differentially expressed through splicing in pathological situations and in the healthy situation. These splicing events may be specific of a given stage in the development of the disease or characteristic of the healthy state.

Comparison of these sequences with databases makes it possible to classify the information obtained and propose a reasoned selection of sequences according to their diagnostic or therapeutic interest.

The performance of DATAS on RNAs from 60-day-old transgenic and control animals has led to the isolation of a cDNA fragment derived from phosphodiesterase 4B mRNA. This fragment corresponds to an exon fragment specifically present in control animals and therefore specifically deleted in SOD1G93A transgenic animals at the 60-day-old stage. The fragment runs from nucleotides 377 to 486 numbered from the stop codon of murine PDE4B (SEQ ID NO:1). This sequence comprises 2912 bases, the deleted fragment corresponding to bases 2760 to 2869. This region is noncoding and is expressed differentially between control animals and transgenic animals, due to alternative use of a 3' noncoding exon and due to the use of two alternative polyadenylation sites.

Example 2
RT-PCR Experiments: Confirmation of Differential Expression

Figure 2:
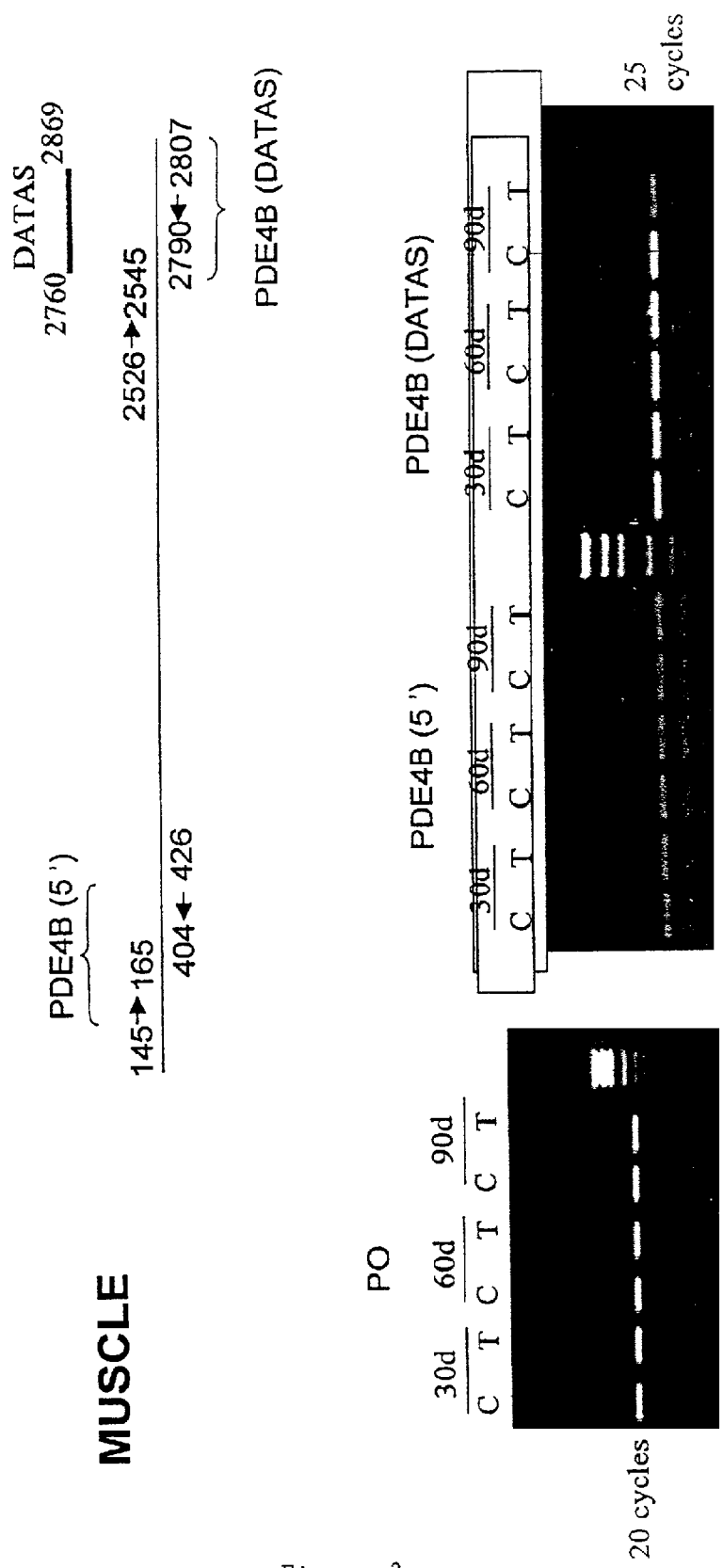
FIG. 2: Semi-quantitative PCR of PDE4B on muscle specimens.

Differential expression of PDE4B in a situation of neuronal stress, as compared to a reference situation, was demonstrated by the RT-PCR experiments described in FIGS. 1 and 2.

These experiments were conducted according to methods well known to those skilled in the art and made it possible to follow the expressions of two distinct regions of PDE4B mRNA. One such region spans the initiation codon of this mRNA (PDE4B 5'), the other partly spans the fragment identified by the DATAS method (PDE4B DATAS). The locations of the PCR primers used are indicated in FIGS. 1 and 2.

PO RNA is a ribosomal RNA used as internal control to check that the same amount of RNA was used for each experimental point. Analyses were performed with RNA extracted from control (c) and transgenic (T) animals aged 30, 60 and 90 days, i.e. before onset of pathological symptoms. FIG. 1 shows the results obtained from RNA extracted from the animals' brains.

Whereas the same quantity of cDNA is amplified from PO RNA in all samples, variations are seen with PDE4B mRNA. The most significant variations are detected in the 90-day-old animals: while an increase in the expression of the PDE4 5' fragment is observed in brain of transgenic animals, a very strong decrease in PDE4B expression (DATAS) occurs in the brain of transgenic animals.

This finding establishes a correlation between the decrease in expression of a 3' noncoding mRNA fragment of PDE4B and the increase in expression of the 5' coding region of this same messenger. This result is altogether compatible with the presence of mRNA destabilising sequences in the sequence identified by DATAS and demonstrates the correlation between PDE4B expression and the phenomenon of excitotoxicity.

Example 3
Inhibition of Excitotoxicity by Inhibitors of PDE4

For this example, rat brain granular neurons were cultured according to methods known to those skilled in the art. Excitotoxicity was induced in these cells by two types of treatment: combined administration of 100 $\mu$M NMDA (N-Methyl-D-apartic acid) and 10 $\mu$M serine on the one hand, administration of 50 $\mu$M kainate on the other hand. Under the experimental conditions used, 30 to 40% toxicity is observed and measured by MTT tests known to those skilled in the art.

Figure 3:
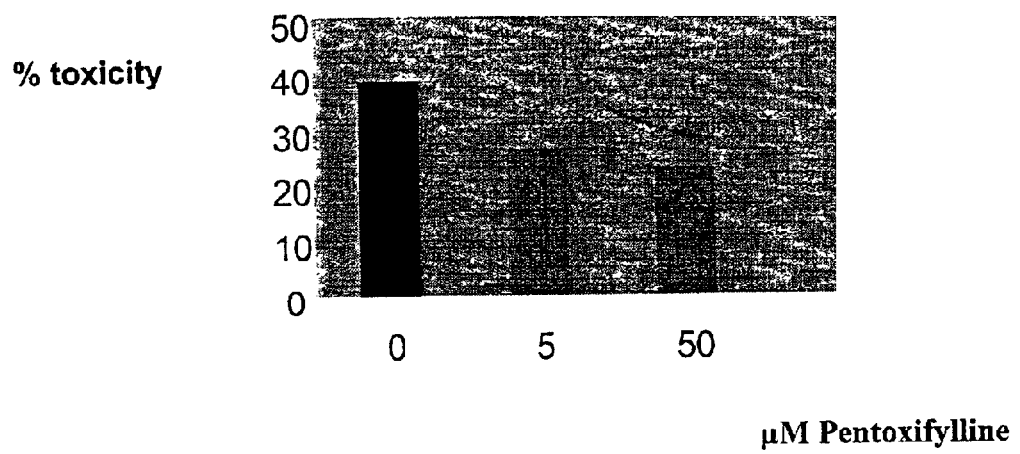
FIG. 3: Pentoxifylline protects primary neurons against formation of cerebellar inclusions related to excitotoxicity induced by 100 $\mu$M NMDA/10 $\mu$M serine and by 50 $\mu$M kainate.
Figure 3:
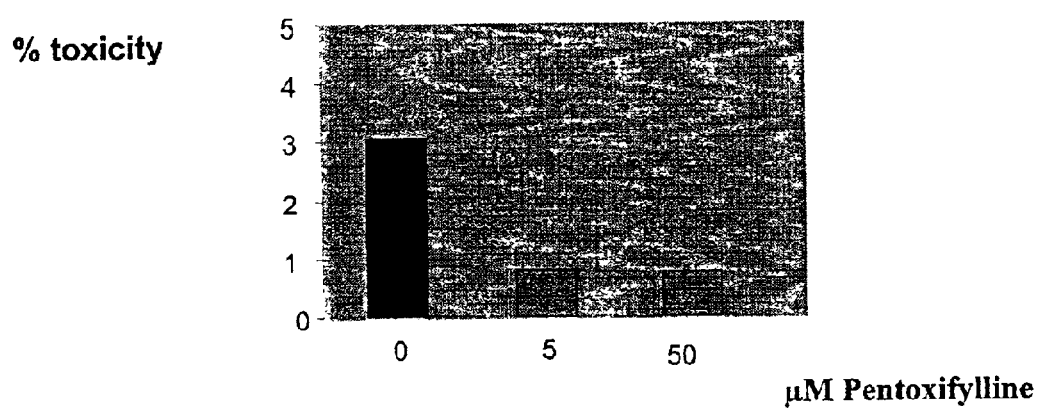

During cotreatment of neurons with a PDE4 inhibitor, a dose-dependent protective effect is observed for both modes of excitotoxicity induction. Such a protective effect is seen with pentoxifylline, etazolate and denbufylline. FIG. 3 presents the results obtained with pentoxifylline which affords 50% protection after NMDA/serine treatment and 80% for kainate-induced toxicity (FIG. 3). The present invention therefore not only demonstrates the involvement of PDE4B in mechanisms of excitotoxicity, particularly in an ALS model, but also demonstrates the ability of PDE4 inhibitors to preserve neuronal viability during stress linked to excitotoxicity.

Other aspects and applications of the invention concern:

use of all or part of a sequence derived from PDE4B messenger RNA for purposes of diagnosis or screening or characterisation of neurodegenerative diseases having a component or a stage related to the excitotoxicity phenomenon, such as Alzheimer's disease, Parkinson's disease, multiple sclerosis, Huntington's chorea and cerebral ischemia, use of any nucleic acid fragment including antisense RNAs for purposes of inhibiting expression of PDE4B in patients with such diseases, use of any chemical compound, notably pentoxifylline or etazolate, or any pharmaceutical composition containing them, for purposes of inhibiting PDE4B activity in patients with such diseases, use of all or part of a sequence derived from PDE4B messenger RNA for purposes of characterising tissue and the ischemic situation.

What is claimed is:

1. A method for the treatment of Amyotropic Lateral Sclerosis, comprising administering to a subject in need thereof a compound selected from the group consisting of pentoxifylline and etazolate.

2. A method according to claim 1, comprising administering to said subject an effective amount of pentoxifylline.

3. A method according to claim 1, comprising administering to said subject an effective amount of etazolate.

4. The method of claim 1 wherein said treatment reduces neuronal excitotoxicity at the early stage of Amyotropic Lateral Sclerosis.

5. The method of claim 2 wherein said treatment reduces neuronal excitotoxicity at the early stage of Amyotropic Lateral Sclerosis.

6. The method of claim 3 wherein said treatment reduces neuronal excitotoxicity at the early stage of Amyotropic Lateral Sclerosis.

7. A method for reducing early neuronal excitotoxicity associated with Amyotrophic Lateral Sclerosis, comprising administering to a subject in need thereof an effective amount of a compound selected from the group consisting of pentoxifylline and etazolate.

* * * * *

SEQUENCE LISTING

<160> NUMBER OF SEQ ID NOS: 4

<210> SEQ ID NO 1
<211> LENGTH: 2912
<212> TYPE: DNA
<213> ORGANISM: souris
<220> FEATURE:
<221> NAME/KEY: CDS
<222> LOCATION: (218)..(2383)

<400> SEQUENCE: 1

```
aaaggcagcc tgataaagct ccttgtgaca ggctgtcttg ccagtctccc agtatgctcc      60
tcttgctctg aagtgctcca ggattgaaac cacagcttcc caaattagcc tgggaagagt     120
gtgcggaccc agcagccttt taacccgcgt cagtgccttt gctatgttca agactgctgt     180
tttggatggt gaatgctagc tagcactcca tcgagac atg aca gca aaa aat tct     235
                                          Met Thr Ala Lys Asn Ser
                                            1               5 cca aaa gaa ttt act gct tcg gaa tct gag gtt tgc ata aag act ttc     283
Pro Lys Glu Phe Thr Ala Ser Glu Ser Glu Val Cys Ile Lys Thr Phe
             10                  15                  20 aag gag cag atg cgc ttg gaa ctt gag ctt cca aag cta cca gga aac     331
Lys Glu Gln Met Arg Leu Glu Leu Glu Leu Pro Lys Leu Pro Gly Asn
         25                  30                  35 aga cct aca tct ccc aaa att tct cca cgc agt tca cca agg aat tca     379
Arg Pro Thr Ser Pro Lys Ile Ser Pro Arg Ser Ser Pro Arg Asn Ser
     40                  45                  50 cca tgc ttt ttc aga aag ttg ctg gtg aat aaa agc atc cga cag cgg     427
Pro Cys Phe Phe Arg Lys Leu Leu Val Asn Lys Ser Ile Arg Gln Arg
 55                  60                  65                  70 cgt cgc ttc acg gtg gct cat aca tgc ttt gat gtg gaa aat ggc cct     475
Arg Arg Phe Thr Val Ala His Thr Cys Phe Asp Val Glu Asn Gly Pro
                 75                  80                  85 tct cca ggt cgg agc cca ctg gac cct caa gcc ggc tct tcg tcg gga     523
Ser Pro Gly Arg Ser Pro Leu Asp Pro Gln Ala Gly Ser Ser Ser Gly
             90                  95                 100 ctg gta ctt cat gcc gcc ttt cct ggg cac agc cag cgc agg gag tcg     571
Leu Val Leu His Ala Ala Phe Pro Gly His Ser Gln Arg Arg Glu Ser
        105                 110                 115 ttc ctc tac gat ctt gac agc gac tat gac ttg tca cca aaa gcg atg     619
Phe Leu Tyr Asp Leu Asp Ser Asp Tyr Asp Leu Ser Pro Lys Ala Met
    120                 125                 130 tcc agg aac tca tca ctt ccc agt gag caa cac ggc gat gac ctg att     667
Ser Arg Asn Ser Ser Leu Pro Ser Glu Gln His Gly Asp Asp Leu Ile
135                 140                 145                 150
```

```
gtc act cct ttt gcc cag gtt ctt gcc agc ttg cga agt gta aga aac      715
Val Thr Pro Phe Ala Gln Val Leu Ala Ser Leu Arg Ser Val Arg Asn
            155                 160                 165 aac ttc acc ctg ctg acg aac ctt cat gga gcg ccg aac aag agg tca      763
Asn Phe Thr Leu Leu Thr Asn Leu His Gly Ala Pro Asn Lys Arg Ser
        170                 175                 180 cca gcg gct agt cag gct cca gtc tcc aga gtc agc ctg caa gag gaa      811
Pro Ala Ala Ser Gln Ala Pro Val Ser Arg Val Ser Leu Gln Glu Glu
            185                 190                 195 tca tat cag aaa cta gca atg gag acg ctg gag gaa cta gac tgg tgc      859
Ser Tyr Gln Lys Leu Ala Met Glu Thr Leu Glu Glu Leu Asp Trp Cys
        200                 205                 210 cta gac cag cta gag acc atc cag acc tac cgc tct gtc agc gag atg      907
Leu Asp Gln Leu Glu Thr Ile Gln Thr Tyr Arg Ser Val Ser Glu Met
215                 220                 225                 230 gct tca aac aag ttc aaa agg atg ctg aac cgg gag ctg aca cac ctc      955
Ala Ser Asn Lys Phe Lys Arg Met Leu Asn Arg Glu Leu Thr His Leu
        235                 240                 245 tca gag atg agc aga tca ggg aac cag gtg tct gag tac att tca aac     1003
Ser Glu Met Ser Arg Ser Gly Asn Gln Val Ser Glu Tyr Ile Ser Asn
            250                 255                 260 acg ttc tta gac aag cag aac gat gtg gaa atc cca tct ccc acg cag     1051
Thr Phe Leu Asp Lys Gln Asn Asp Val Glu Ile Pro Ser Pro Thr Gln
        265                 270                 275 aag gac agg gag aag aag aag cag cag ctc atg acc cag ata agt         1099
Lys Asp Arg Glu Lys Lys Lys Gln Gln Leu Met Thr Gln Ile Ser
    280                 285                 290 gga gtg aag aaa ctg atg cac agc tca agc ctg aac aac aca agc atc     1147
Gly Val Lys Lys Leu Met His Ser Ser Ser Leu Asn Asn Thr Ser Ile
295                 300                 305                 310 tca cgc ttc ggg atc aac acg gaa aat gag gat cat cta gcc aag gag     1195
Ser Arg Phe Gly Ile Asn Thr Glu Asn Glu Asp His Leu Ala Lys Glu
            315                 320                 325 ctg gaa gac ctg aac aaa tgg ggc ctt aac atc ttc aat gtg gct ggg     1243
Leu Glu Asp Leu Asn Lys Trp Gly Leu Asn Ile Phe Asn Val Ala Gly
        330                 335                 340 tac tca cat aat cgg ccc ctt acg tgc atc atg tat gca ata ttc cag     1291
Tyr Ser His Asn Arg Pro Leu Thr Cys Ile Met Tyr Ala Ile Phe Gln
            345                 350                 355 gaa aga gac ctt ctg aag acg ttt aaa atc tca tct gac acc ttt gta     1339
Glu Arg Asp Leu Leu Lys Thr Phe Lys Ile Ser Ser Asp Thr Phe Val
        360                 365                 370 acc tac atg atg act tta gaa gac cat tac cat tct gat gtg gca tat     1387
Thr Tyr Met Met Thr Leu Glu Asp His Tyr His Ser Asp Val Ala Tyr
375                 380                 385                 390 cac aac agc ctg cat gct gct gac gtg gcc cag tca act cac gtt ctc     1435
His Asn Ser Leu His Ala Ala Asp Val Ala Gln Ser Thr His Val Leu
            395                 400                 405 ctt tct acg ccg gca ctg gat gct gtc ttc aca gac ctg gaa atc ctg     1483
Leu Ser Thr Pro Ala Leu Asp Ala Val Phe Thr Asp Leu Glu Ile Leu
        410                 415                 420 gct gcc att ttt gca gct gcc atc cat gat gtc gat cat cct gga gtc     1531
Ala Ala Ile Phe Ala Ala Ala Ile His Asp Val Asp His Pro Gly Val
            425                 430                 435 tcc aat cag ttt ctc atc aat aca aat tct gaa ctt gct ttg atg tat    1579
Ser Asn Gln Phe Leu Ile Asn Thr Asn Ser Glu Leu Ala Leu Met Tyr
        440                 445                 450 aat gat gaa tct gtt ctg gaa aac cat cac ctt gct gtg gga ttc aaa    1627
Asn Asp Glu Ser Val Leu Glu Asn His His Leu Ala Val Gly Phe Lys
```

-continued

```
                455                 460                 465                 470
ttg cta caa gag gaa cac tgc gac atc ttt cag aat ctt acc aag aag         1675
Leu Leu Gln Glu Glu His Cys Asp Ile Phe Gln Asn Leu Thr Lys Lys
                        475                 480                 485 caa cgc cag aca ctc agg aaa atg gtg att gac atg gtg ttg gca act         1723
Gln Arg Gln Thr Leu Arg Lys Met Val Ile Asp Met Val Leu Ala Thr
            490                 495                 500 gat atg tcc aaa cac atg agc ctc ctg gca gac ctt aaa aca atg gta         1771
Asp Met Ser Lys His Met Ser Leu Leu Ala Asp Leu Lys Thr Met Val
                505                 510                 515 gaa acc aag aag gtg aca agc tcc ggt gtt ctc ctc ctg gac aac tat         1819
Glu Thr Lys Lys Val Thr Ser Ser Gly Val Leu Leu Leu Asp Asn Tyr
        520                 525                 530 act gac cgg ata cag gtt ctt cgc aac atg gta cac tgt gca gac ctg         1867
Thr Asp Arg Ile Gln Val Leu Arg Asn Met Val His Cys Ala Asp Leu
535                 540                 545                 550 agc aac ccc acc aag tcc ttg gaa ttg tat cgg caa tgg acc gat cgt         1915
Ser Asn Pro Thr Lys Ser Leu Glu Leu Tyr Arg Gln Trp Thr Asp Arg
                    555                 560                 565 atc atg gag gag ttt ttc cag cag gga gac aaa gaa cgg gag agg gga         1963
Ile Met Glu Glu Phe Phe Gln Gln Gly Asp Lys Glu Arg Glu Arg Gly
                570                 575                 580 atg gag att agc cca atg tgt gat aag cac aca gct tct gtg gaa aaa         2011
Met Glu Ile Ser Pro Met Cys Asp Lys His Thr Ala Ser Val Glu Lys
            585                 590                 595 tcc cag gtt ggt ttc att gac tac att gtc cat cca ctg tgg gag acc         2059
Ser Gln Val Gly Phe Ile Asp Tyr Ile Val His Pro Leu Trp Glu Thr
        600                 605                 610 tgg gca gac ctg gtt caa ccg gat gct caa gat att ctg gat aca cta         2107
Trp Ala Asp Leu Val Gln Pro Asp Ala Gln Asp Ile Leu Asp Thr Leu
615                 620                 625                 630 gaa gat aac agg aac tgg tac cag agt atg ata ccc cag agc cct tcc         2155
Glu Asp Asn Arg Asn Trp Tyr Gln Ser Met Ile Pro Gln Ser Pro Ser
                    635                 640                 645 ccg cca ctg gat gag agg agc agg gac tgc caa ggc ctg atg gag aag         2203
Pro Pro Leu Asp Glu Arg Ser Arg Asp Cys Gln Gly Leu Met Glu Lys
                650                 655                 660 ttt cag ttt gaa ctg acc ctt gag gaa gag gat tct gag gga ccg gaa         2251
Phe Gln Phe Glu Leu Thr Leu Glu Glu Glu Asp Ser Glu Gly Pro Glu
            665                 670                 675 aag gag gga gaa ggc cac agc tat ttc agc agc aca aag acg ctt tgt         2299
Lys Glu Gly Glu Gly His Ser Tyr Phe Ser Ser Thr Lys Thr Leu Cys
        680                 685                 690 gtg att gat cca gag aac agg gat tct ctg gaa gag act gac ata gac         2347
Val Ile Asp Pro Glu Asn Arg Asp Ser Leu Glu Glu Thr Asp Ile Asp
695                 700                 705                 710 att gca aca gaa gac aag tct ccg atc gac aca taa tctctctccc              2393
Ile Ala Thr Glu Asp Lys Ser Pro Ile Asp Thr
                715                 720 tctgtgtgga gatgaacatt ccacccttga ctgagcatgc ccgctgagtg gtagggtcac       2453
ctaccatggc caaggcctgc acaggacaaa ggccacctgg cctttccagt tacttgagtt       2513
tggagccaga atgccaggcc gtgaagcaaa tagcagttcc atgctgtctt gccttgcctg       2573
caagcttggc ggagacccgc agctgtatgt ggtagtagag gccagttccc atcaaagcta       2633
aaatggcttg aaaacagagg acacaaagct gagagattgc tctgcactag gtgttgggaa       2693
gctgtcctga cagatgactg aactcactaa caacttcatc tataaatctc accacccaac       2753
ccattgtctg ccaacctgtg tgccttttttt tgtaaaatgt tttcgcgtct ttgaaatgcc      2813
```

```
tgttgaatat ctagagttta gtaccaactt ctacaaactt ttttgagtct ttcttgaaaa    2873
acaaaaaaaa aaaaaaaaaa aaaaaaaaaa aaaaaaaaa                           2912
```

<210> SEQ ID NO 2
<211> LENGTH: 721
<212> TYPE: PRT
<213> ORGANISM: souris

<400> SEQUENCE: 2

```
Met Thr Ala Lys Asn Ser Pro Lys Glu Phe Thr Ala Ser Glu Ser Glu
 1               5                  10                  15

Val Cys Ile Lys Thr Phe Lys Glu Gln Met Arg Leu Glu Leu Glu Leu
            20                  25                  30

Pro Lys Leu Pro Gly Asn Arg Pro Thr Ser Pro Lys Ile Ser Pro Arg
        35                  40                  45

Ser Ser Pro Arg Asn Ser Pro Cys Phe Phe Arg Lys Leu Leu Val Asn
    50                  55                  60

Lys Ser Ile Arg Gln Arg Arg Phe Thr Val Ala His Thr Cys Phe
65                  70                  75                  80

Asp Val Glu Asn Gly Pro Ser Pro Gly Arg Ser Pro Leu Asp Pro Gln
                85                  90                  95

Ala Gly Ser Ser Gly Leu Val Leu His Ala Ala Phe Pro Gly His
            100                 105                 110

Ser Gln Arg Arg Glu Ser Phe Leu Tyr Asp Leu Asp Ser Asp Tyr Asp
        115                 120                 125

Leu Ser Pro Lys Ala Met Ser Arg Asn Ser Ser Leu Pro Ser Glu Gln
    130                 135                 140

His Gly Asp Asp Leu Ile Val Thr Pro Phe Ala Gln Val Leu Ala Ser
145                 150                 155                 160

Leu Arg Ser Val Arg Asn Asn Phe Thr Leu Leu Thr Asn Leu His Gly
                165                 170                 175

Ala Pro Asn Lys Arg Ser Pro Ala Ala Ser Gln Ala Pro Val Ser Arg
            180                 185                 190

Val Ser Leu Gln Glu Glu Ser Tyr Gln Lys Leu Ala Met Glu Thr Leu
        195                 200                 205

Glu Glu Leu Asp Trp Cys Leu Asp Gln Leu Glu Thr Ile Gln Thr Tyr
    210                 215                 220

Arg Ser Val Ser Glu Met Ala Ser Asn Lys Phe Lys Arg Met Leu Asn
225                 230                 235                 240

Arg Glu Leu Thr His Leu Ser Glu Met Ser Arg Ser Gly Asn Gln Val
                245                 250                 255

Ser Glu Tyr Ile Ser Asn Thr Phe Leu Asp Lys Gln Asn Asp Val Glu
            260                 265                 270

Ile Pro Ser Pro Thr Gln Lys Asp Arg Glu Lys Lys Lys Gln Gln
        275                 280                 285

Leu Met Thr Gln Ile Ser Gly Val Lys Lys Leu Met His Ser Ser Ser
    290                 295                 300

Leu Asn Asn Thr Ser Ile Ser Arg Phe Gly Ile Asn Thr Glu Asn Glu
305                 310                 315                 320

Asp His Leu Ala Lys Glu Leu Glu Asp Leu Asn Lys Trp Gly Leu Asn
                325                 330                 335

Ile Phe Asn Val Ala Gly Tyr Ser His Asn Arg Pro Leu Thr Cys Ile
            340                 345                 350
```

```
Met Tyr Ala Ile Phe Gln Glu Arg Asp Leu Leu Lys Thr Phe Lys Ile
        355                 360                 365

Ser Ser Asp Thr Phe Val Thr Tyr Met Met Thr Leu Glu Asp His Tyr
        370                 375                 380

His Ser Asp Val Ala Tyr His Asn Ser Leu His Ala Ala Asp Val Ala
385                 390                 395                 400

Gln Ser Thr His Val Leu Leu Ser Thr Pro Ala Leu Asp Ala Val Phe
                405                 410                 415

Thr Asp Leu Glu Ile Leu Ala Ala Ile Phe Ala Ala Ile His Asp
        420                 425                 430

Val Asp His Pro Gly Val Ser Asn Gln Phe Leu Ile Asn Thr Asn Ser
        435                 440                 445

Glu Leu Ala Leu Met Tyr Asn Asp Glu Ser Val Leu Glu Asn His His
        450                 455                 460

Leu Ala Val Gly Phe Lys Leu Leu Gln Glu Glu His Cys Asp Ile Phe
465                 470                 475                 480

Gln Asn Leu Thr Lys Lys Gln Arg Gln Thr Leu Arg Lys Met Val Ile
                485                 490                 495

Asp Met Val Leu Ala Thr Asp Met Ser Lys His Met Ser Leu Leu Ala
                500                 505                 510

Asp Leu Lys Thr Met Val Glu Thr Lys Lys Val Thr Ser Ser Gly Val
        515                 520                 525

Leu Leu Leu Asp Asn Tyr Thr Asp Arg Ile Gln Val Leu Arg Asn Met
        530                 535                 540

Val His Cys Ala Asp Leu Ser Asn Pro Thr Lys Ser Leu Glu Leu Tyr
545                 550                 555                 560

Arg Gln Trp Thr Asp Arg Ile Met Glu Glu Phe Phe Gln Gln Gly Asp
                565                 570                 575

Lys Glu Arg Glu Arg Gly Met Glu Ile Ser Pro Met Cys Asp Lys His
                580                 585                 590

Thr Ala Ser Val Glu Lys Ser Gln Val Gly Phe Ile Asp Tyr Ile Val
        595                 600                 605

His Pro Leu Trp Glu Thr Trp Ala Asp Leu Val Gln Pro Asp Ala Gln
        610                 615                 620

Asp Ile Leu Asp Thr Leu Glu Asp Asn Arg Asn Trp Tyr Gln Ser Met
625                 630                 635                 640

Ile Pro Gln Ser Pro Ser Pro Leu Asp Glu Arg Ser Arg Asp Cys
                645                 650                 655

Gln Gly Leu Met Glu Lys Phe Gln Phe Glu Leu Thr Leu Glu Glu Glu
                660                 665                 670

Asp Ser Glu Gly Pro Glu Lys Glu Gly Glu Gly His Ser Tyr Phe Ser
                675                 680                 685

Ser Thr Lys Thr Leu Cys Val Ile Asp Pro Glu Asn Arg Asp Ser Leu
        690                 695                 700

Glu Glu Thr Asp Ile Asp Ile Ala Thr Glu Asp Lys Ser Pro Ile Asp
705                 710                 715                 720

Thr

<210> SEQ ID NO 3
<211> LENGTH: 4068
<212> TYPE: DNA
<213> ORGANISM: Homo sapiens
<220> FEATURE:
<221> NAME/KEY: CDS
<222> LOCATION: (766)..(2460)
```

<223> OTHER INFORMATION: PDE4B

<400> SEQUENCE: 3

| | |
|---|---|
| gaattcctcc tctcttcacc ccgttagctg ttttcaatgt aatgctgccg tccttctctt | 60 |
| gcactgcctt ctgcgctaac acctccattc ctgtttataa ccgtgtattt attacttaat | 120 |
| gtatataatg taatgttttg taagttatta atttatatat ctaacattgc ctgccaatgg | 180 |
| tggtgttaaa tttgtgtaga aaactctgcc taagagttac gacttttcct tgtaatgttt | 240 |
| tgtattgtgt attatataac ccaaacgtca cttagtagag acatatggcc cccttggcag | 300 |
| agaggacagg ggtgggcttt tgttcaaagg gtctgccctt tccctgcctg agttgctact | 360 |
| tctgcacaac cccttttatga accagttttc acccgaattt tgactgtttc atttagaaga | 420 |
| aaagcaaaat gagaaaaagc tttcctcatt tctccttgag atggcaaagc actcagaaat | 480 |
| gacatcacat accctaaaga accctgggat gactaaggca gagagagtct gagaaaactc | 540 |
| tttggtgctt ctgcctttag ttttaggaca catttatgca gatgagctta taagagaccg | 600 |
| ttccctccgc cttcttcctc agaggaagtt tcttggtaga tcaccgacac ctcatccagg | 660 |
| cgggggggttg ggggggaaact tggcaccagc catcccaggc agagcaccac tgtgatttgt | 720 |
| tctcctggtg gagagagctg aaggaagga gccagcgtgc aaata atg aag gag cac | 777 |
| Met Lys Glu His | |
| 1 | |
| ggg ggc acc ttc agt agc acc gga atc agc ggt ggt agc ggt gac tct | 825 |
| Gly Gly Thr Phe Ser Ser Thr Gly Ile Ser Gly Gly Ser Gly Asp Ser | |
| 5 10 15 20 | |
| gct atg gac agc ctg cag ccg ctc cag cct aac tac atg cct gtg tgt | 873 |
| Ala Met Asp Ser Leu Gln Pro Leu Gln Pro Asn Tyr Met Pro Val Cys | |
| 25 30 35 | |
| ttg ttt gca gaa gaa tct tat caa aaa tta gca atg gaa acg ctg gag | 921 |
| Leu Phe Ala Glu Glu Ser Tyr Gln Lys Leu Ala Met Glu Thr Leu Glu | |
| 40 45 50 | |
| gaa tta gac tgg tgt tta gac cag cta gag acc ata cag acc tac cgg | 969 |
| Glu Leu Asp Trp Cys Leu Asp Gln Leu Glu Thr Ile Gln Thr Tyr Arg | |
| 55 60 65 | |
| tct gtc agt gag atg gct tct aac aag ttc aaa aga atg ctg aac cgg | 1017 |
| Ser Val Ser Glu Met Ala Ser Asn Lys Phe Lys Arg Met Leu Asn Arg | |
| 70 75 80 | |
| gag ctg aca cac ctc tca gag atg agc cga tca ggg aac cag gtg tct | 1065 |
| Glu Leu Thr His Leu Ser Glu Met Ser Arg Ser Gly Asn Gln Val Ser | |
| 85 90 95 100 | |
| gaa tac att tca aat act ttc tta gac aag cag aat gat gtg gag atc | 1113 |
| Glu Tyr Ile Ser Asn Thr Phe Leu Asp Lys Gln Asn Asp Val Glu Ile | |
| 105 110 115 | |
| cca tct cct acc cag aaa gac agg gag aaa aag aaa cag cag ctc | 1161 |
| Pro Ser Pro Thr Gln Lys Asp Arg Glu Lys Lys Lys Gln Gln Leu | |
| 120 125 130 | |
| atg acc cag ata agt gga gtg aag aaa tta atg cat agt tca agc cta | 1209 |
| Met Thr Gln Ile Ser Gly Val Lys Lys Leu Met His Ser Ser Ser Leu | |
| 135 140 145 | |
| aac aat aca agc atc tca cgc ttt gga gtc aac act gaa aat gaa gat | 1257 |
| Asn Asn Thr Ser Ile Ser Arg Phe Gly Val Asn Thr Glu Asn Glu Asp | |
| 150 155 160 | |
| cac ctg gcc aag gag ctg gaa gac ctg aac aaa tgg ggt ctt aac atc | 1305 |
| His Leu Ala Lys Glu Leu Glu Asp Leu Asn Lys Trp Gly Leu Asn Ile | |
| 165 170 175 180 | |
| ttt aat gtg gct gga tat tct cac aat aga ccc cta aca tgc atc atg | 1353 |
| Phe Asn Val Ala Gly Tyr Ser His Asn Arg Pro Leu Thr Cys Ile Met | |
| 185 190 195 | |

-continued

```
tat gct ata ttc cag gaa aga gac ctc cta aag aca ttc aga atc tca      1401
Tyr Ala Ile Phe Gln Glu Arg Asp Leu Leu Lys Thr Phe Arg Ile Ser
        200                 205                 210 tct gac aca ttt ata acc tac atg atg act tta gaa gac cat tac cat      1449
Ser Asp Thr Phe Ile Thr Tyr Met Met Thr Leu Glu Asp His Tyr His
            215                 220                 225 tct gac gtg gca tat cac aac agc ctg cac gct gct gat gta gcc cag      1497
Ser Asp Val Ala Tyr His Asn Ser Leu His Ala Ala Asp Val Ala Gln
        230                 235                 240 tcg acc cat gtt ctc ctt tct aca cca gca tta gac gct gtc ttc aca      1545
Ser Thr His Val Leu Leu Ser Thr Pro Ala Leu Asp Ala Val Phe Thr
245                 250                 255                 260 gat ttg gag atc ctg gct gcc att ttt gca gct gcc atc cat gac gtt      1593
Asp Leu Glu Ile Leu Ala Ala Ile Phe Ala Ala Ala Ile His Asp Val
                265                 270                 275 gat cat cct gga gtc tcc aat cag ttt ctc atc aac aca aat tca gaa      1641
Asp His Pro Gly Val Ser Asn Gln Phe Leu Ile Asn Thr Asn Ser Glu
            280                 285                 290 ctt gct ttg atg tat aat gat gaa tct gtg ttg gaa aat cat cac ctt      1689
Leu Ala Leu Met Tyr Asn Asp Glu Ser Val Leu Glu Asn His His Leu
        295                 300                 305 gct gtg ggt ttc aaa ctg ctg caa gaa gaa cac tgt gac atc ttc atg      1737
Ala Val Gly Phe Lys Leu Leu Gln Glu Glu His Cys Asp Ile Phe Met
    310                 315                 320 aat ctc acc aag aag cag cgt cag aca ctc agg aag atg gtt att gac      1785
Asn Leu Thr Lys Lys Gln Arg Gln Thr Leu Arg Lys Met Val Ile Asp
325                 330                 335                 340 atg gtg tta gca act gat atg tct aaa cat atg agc ctg ctg gca gac      1833
Met Val Leu Ala Thr Asp Met Ser Lys His Met Ser Leu Leu Ala Asp
                345                 350                 355 ctg aag aca atg gta gaa acg aag aaa gtt aca agt tca ggc gtt ctt      1881
Leu Lys Thr Met Val Glu Thr Lys Lys Val Thr Ser Ser Gly Val Leu
            360                 365                 370 ctc cta gac aac tat acc gat cgc att cag gtc ctt cgc aac atg gta      1929
Leu Leu Asp Asn Tyr Thr Asp Arg Ile Gln Val Leu Arg Asn Met Val
        375                 380                 385 cac tgt gca gac ctg agc aac ccc acc aag tcc ttg gaa ttg tat cgg      1977
His Cys Ala Asp Leu Ser Asn Pro Thr Lys Ser Leu Glu Leu Tyr Arg
    390                 395                 400 caa tgg aca gac cgc atc atg gag gaa ttt ttc cag cag gga gac aaa      2025
Gln Trp Thr Asp Arg Ile Met Glu Glu Phe Phe Gln Gln Gly Asp Lys
405                 410                 415                 420 gag cgg gag agg gga atg gaa att agc cca atg tgt gat aaa cac aca      2073
Glu Arg Glu Arg Gly Met Glu Ile Ser Pro Met Cys Asp Lys His Thr
                425                 430                 435 gct tct gtg gaa aaa tcc cag gtt ggt ttc atc gac tac att gtc cat      2121
Ala Ser Val Glu Lys Ser Gln Val Gly Phe Ile Asp Tyr Ile Val His
            440                 445                 450 cca ttg tgg gag aca tgg gca gat ttg gta cag cct gat gct cag gac      2169
Pro Leu Trp Glu Thr Trp Ala Asp Leu Val Gln Pro Asp Ala Gln Asp
        455                 460                 465 att ctc gat acc tta gaa gat aac agg aac tgg tat cag agc atg ata      2217
Ile Leu Asp Thr Leu Glu Asp Asn Arg Asn Trp Tyr Gln Ser Met Ile
    470                 475                 480 cct caa agt ccc tca cca cca ctg gac gag cag aac agg gac tgc cag      2265
Pro Gln Ser Pro Ser Pro Pro Leu Asp Glu Gln Asn Arg Asp Cys Gln
485                 490                 495                 500 ggt ctg atg gag aag ttt cag ttt gaa ctg act ctc gat gag gaa gat      2313
Gly Leu Met Glu Lys Phe Gln Phe Glu Leu Thr Leu Asp Glu Glu Asp
```

|  |  |  |  |  |  |  |  |  |  |  |  |  |  |  |  |
|---|---|---|---|---|---|---|---|---|---|---|---|---|---|---|---|
|  |  | 505 |  |  |  | 510 |  |  |  |  | 515 |  |  |  |  |
| tct | gaa | gga | cct | gag | aag | gag | gga | gag | gga | cac | agc | tat | ttc | agc | agc |
| Ser | Glu | Gly | Pro | Glu | Lys | Glu | Gly | Glu | Gly | His | Ser | Tyr | Phe | Ser | Ser |
|  |  | 520 |  |  |  | 525 |  |  |  |  | 530 |  |  |  |  |

2361

|  |  |  |  |  |  |  |  |  |  |  |  |  |  |  |  |
|---|---|---|---|---|---|---|---|---|---|---|---|---|---|---|---|
| aca | aag | acg | ctt | tgt | gtg | att | gat | cca | gaa | aac | aga | gat | tcc | ctg | gga |
| Thr | Lys | Thr | Leu | Cys | Val | Ile | Asp | Pro | Glu | Asn | Arg | Asp | Ser | Leu | Gly |
|  |  |  | 535 |  |  |  |  | 540 |  |  |  |  | 545 |  |  |

2409

|  |  |  |  |  |  |  |  |  |  |  |  |  |  |  |  |
|---|---|---|---|---|---|---|---|---|---|---|---|---|---|---|---|
| gag | act | gac | ata | gac | att | gca | aca | gaa | gac | aag | tcc | ccc | gtg | gat | aca |
| Glu | Thr | Asp | Ile | Asp | Ile | Ala | Thr | Glu | Asp | Lys | Ser | Pro | Val | Asp | Thr |
|  | 550 |  |  |  |  | 555 |  |  |  |  | 560 |  |  |  |  |

2457

| | |
|---|---|
| taa tcccctctc cctgtggaga tgaacattct atccttgatg agcatgccag | 2510 |
| ctatgtggta gggccagccc accatggggg ccaagacctg cacaggacaa gggccacctg | 2570 |
| gcctttcagt tacttgagtt tggagtcaga aagcaagacc aggaagcaaa tagcagctca | 2630 |
| ggaaatccca cggttgactt gccttgatgg caagcttggt ggagagggct gaagctgttg | 2690 |
| ctggggccg attctgatca agacacatgg cttgaaaatg gaagcacaa aactgagaga | 2750 |
| tcattctgca ctaagtttcg ggaacttatc cccgacagtg actgaactca ctgactaata | 2810 |
| acttcattta tgaatcttct cacttgtccc tttgtctgcc aacctgtgtg ccttttttgt | 2870 |
| aaaacatttt catgtcttta aaatgcctgt tgaatacctg gagtttagta tcaacttcta | 2930 |
| cacagataag ctttcaaagt tgacaaactt ttttgactct ttctggaaaa gggaaagaaa | 2990 |
| atagtcttcc ttctttcttg ggcaatatcc ttcactttac tacagttact tttgcaaaca | 3050 |
| gacagaaagg atacacttct aaccacattt tacttccttc ccctgttgtc cagtccaact | 3110 |
| ccacagtcac tcttaaaact tctctctgtt tgcctgcctc aacagtact tttaacttttt | 3170 |
| tgctgtaaac agaataaaat tgaacaaatt aggggggtaga aaggagcagt ggtgtcgttc | 3230 |
| accgtgagag tctgcataga actcagcagt gtgccctgct gtgtcttgga ccctgccccc | 3290 |
| cacaggagtt gctacagtcc ctggccctgc ttcccatcct cctctcttca ccccgttagc | 3350 |
| tgttttcaat gtaatgctgc cgtccttctc ttgcactgcc ttctgcgcta acacctccat | 3410 |
| tcctgtttat aaccgtgtat ttattactta atgtatataa tgtaatgttt tgtaagttat | 3470 |
| taatttatat atctaacatt gcctgccaat ggtggtgtta aatttgtgta gaaaactctg | 3530 |
| cctaagagtt acgacttttt cttgtaatgt tttgtattgt gtattatata acccaaacgt | 3590 |
| cacttagtag agacatatgg cccccttggc agagaggaca ggggtgggct tttgttcaaa | 3650 |
| gggtctgccc tttccctgcc tgagttgcta cttctgcaca accccttat gaaccagttt | 3710 |
| tggaaacaat attctcacat tagatactaa atggtttata ctgagtcttt tacttttgta | 3770 |
| tagcttgata ggggcagggg caatgggatg tagttttttac ccaggttcta tccaaatcta | 3830 |
| tgtgggcatg agttgggtta taactggatc ctactatcat tgtggctttg gttcaaaagg | 3890 |
| aaacactaca tttgctcaca gatgattctt ctgattcttc tgaatgctcc cgaactactg | 3950 |
| actttgaaga ggtagcctcc tgcctgccat taagcaggaa tgtcatgttc cagttcatta | 4010 |
| caaaagaaaa caataaaaca atgtgaattt ttataataaa aaaaaaaaa aggaattc | 4068 |

<210> SEQ ID NO 4
<211> LENGTH: 564
<212> TYPE: PRT
<213> ORGANISM: Homo sapiens

<400> SEQUENCE: 4

|  |  |  |  |  |  |  |  |  |  |  |  |  |  |  |
|---|---|---|---|---|---|---|---|---|---|---|---|---|---|---|
| Met | Lys | Glu | His | Gly | Gly | Thr | Phe | Ser | Ser | Thr | Gly | Ile | Ser | Gly |
| 1 |  |  |  | 5 |  |  |  |  | 10 |  |  |  |  | 15 |

-continued

```
Ser Gly Asp Ser Ala Met Asp Ser Leu Gln Pro Leu Gln Pro Asn Tyr
             20                  25                  30

Met Pro Val Cys Leu Phe Ala Glu Glu Ser Tyr Gln Lys Leu Ala Met
             35                  40                  45

Glu Thr Leu Glu Glu Leu Asp Trp Cys Leu Asp Gln Leu Glu Thr Ile
 50                  55                  60

Gln Thr Tyr Arg Ser Val Ser Glu Met Ala Ser Asn Lys Phe Lys Arg
 65                  70                  75                  80

Met Leu Asn Arg Glu Leu Thr His Leu Ser Glu Met Ser Arg Ser Gly
             85                  90                  95

Asn Gln Val Ser Glu Tyr Ile Ser Asn Thr Phe Leu Asp Lys Gln Asn
            100                 105                 110

Asp Val Glu Ile Pro Ser Pro Thr Gln Lys Asp Arg Glu Lys Lys Lys
            115                 120                 125

Lys Gln Gln Leu Met Thr Gln Ile Ser Gly Val Lys Lys Leu Met His
130                 135                 140

Ser Ser Ser Leu Asn Asn Thr Ser Ile Ser Arg Phe Gly Val Asn Thr
145                 150                 155                 160

Glu Asn Glu Asp His Leu Ala Lys Glu Leu Asp Leu Asn Lys Trp
            165                 170                 175

Gly Leu Asn Ile Phe Asn Val Ala Gly Tyr Ser His Asn Arg Pro Leu
            180                 185                 190

Thr Cys Ile Met Tyr Ala Ile Phe Gln Glu Arg Asp Leu Leu Lys Thr
            195                 200                 205

Phe Arg Ile Ser Ser Asp Thr Phe Ile Thr Tyr Met Met Thr Leu Glu
210                 215                 220

Asp His Tyr His Ser Asp Val Ala Tyr His Asn Ser Leu His Ala Ala
225                 230                 235                 240

Asp Val Ala Gln Ser Thr His Val Leu Leu Ser Thr Pro Ala Leu Asp
            245                 250                 255

Ala Val Phe Thr Asp Leu Glu Ile Leu Ala Ala Ile Phe Ala Ala Ala
            260                 265                 270

Ile His Asp Val Asp His Pro Gly Val Ser Asn Gln Phe Leu Ile Asn
            275                 280                 285

Thr Asn Ser Glu Leu Ala Leu Met Tyr Asn Asp Glu Ser Val Leu Glu
290                 295                 300

Asn His His Leu Ala Val Gly Phe Lys Leu Leu Gln Glu Glu His Cys
305                 310                 315                 320

Asp Ile Phe Met Asn Leu Thr Lys Lys Gln Arg Gln Thr Leu Arg Lys
            325                 330                 335

Met Val Ile Asp Met Val Leu Ala Thr Asp Met Ser Lys His Met Ser
            340                 345                 350

Leu Leu Ala Asp Leu Lys Thr Met Val Glu Thr Lys Lys Val Thr Ser
            355                 360                 365

Ser Gly Val Leu Leu Leu Asp Asn Tyr Thr Asp Arg Ile Gln Val Leu
            370                 375                 380

Arg Asn Met Val His Cys Ala Asp Leu Ser Asn Pro Thr Lys Ser Leu
385                 390                 395                 400

Glu Leu Tyr Arg Gln Trp Thr Asp Arg Ile Met Glu Glu Phe Phe Gln
            405                 410                 415

Gln Gly Asp Lys Glu Arg Glu Arg Gly Met Glu Ile Ser Pro Met Cys
            420                 425                 430

Asp Lys His Thr Ala Ser Val Glu Lys Ser Gln Val Gly Phe Ile Asp
```

-continued

```
                    435                 440                 445
Tyr Ile Val His Pro Leu Trp Glu Thr Trp Ala Asp Leu Val Gln Pro
    450                 455                 460

Asp Ala Gln Asp Ile Leu Asp Thr Leu Glu Asp Asn Arg Asn Trp Tyr
465                 470                 475                 480

Gln Ser Met Ile Pro Gln Ser Pro Ser Pro Pro Leu Asp Glu Gln Asn
                485                 490                 495

Arg Asp Cys Gln Gly Leu Met Glu Lys Phe Gln Phe Glu Leu Thr Leu
            500                 505                 510

Asp Glu Glu Asp Ser Glu Gly Pro Glu Lys Glu Gly Glu Gly His Ser
        515                 520                 525

Tyr Phe Ser Ser Thr Lys Thr Leu Cys Val Ile Asp Pro Glu Asn Arg
    530                 535                 540

Asp Ser Leu Gly Glu Thr Asp Ile Asp Ile Ala Thr Glu Asp Lys Ser
545                 550                 555                 560

Pro Val Asp Thr
```